US007097857B2

(12) United States Patent
Tracy et al.

(10) Patent No.: US 7,097,857 B2
(45) Date of Patent: *Aug. 29, 2006

(54) METHODS AND COMPOSITIONS FOR THE TARGETED DELIVERY OF BIOLOGICALLY ACTIVE AGENTS

(75) Inventors: Mark A. Tracy, Arlington, MA (US); David S. Scher, Hudson, MA (US)

(73) Assignee: Alkermes Controlled Therapeutics, Inc., Cambridge, MA (US)

(*) Notice: Subject to any disclaimer, the term of this patent is extended or adjusted under 35 U.S.C. 154(b) by 209 days.

This patent is subject to a terminal disclaimer.

(21) Appl. No.: 10/342,448

(22) Filed: Jan. 14, 2003

(65) Prior Publication Data

US 2006/0141041 A1    Jun. 29, 2006

Related U.S. Application Data

(63) Continuation of application No. 09/644,631, filed on Aug. 23, 2000, now Pat. No. 6,565,888.

(51) Int. Cl.
*A61K 9/14* (2006.01)
*A61K 9/00* (2006.01)

(52) U.S. Cl. ............ 424/489; 424/400; 424/490; 424/491; 424/493; 424/497; 424/499

(58) Field of Classification Search ............... 424/400, 424/489, 490, 491, 493, 495, 497, 499
See application file for complete search history.

(56) References Cited

U.S. PATENT DOCUMENTS

| | | |
|---|---|---|
| 4,767,628 A | 8/1988 | Hutchinson |
| 4,919,929 A | 4/1990 | Beck |
| 5,019,400 A | 5/1991 | Gombotz et al. |
| 5,330,768 A | 7/1994 | Park et al. |

(Continued)

FOREIGN PATENT DOCUMENTS

WO    WO 88/01213    2/1988

(Continued)

OTHER PUBLICATIONS

Ando, S., et al., "PLGA Microspheres Containing Plasmid DNA: Preservation of Supercoiled DNA via Cryopreparation and Carbohydrate Stabilization," 88(1):126-129 (1999).

(Continued)

*Primary Examiner*—Michael G. Hartley
*Assistant Examiner*—Simon Oh
(74) *Attorney, Agent, or Firm*—Hamilton, Brook, Smith & Reynolds, P.C.

(57) ABSTRACT

The present invention relates to a sustained release composition for the targeted delivery of biologically active agents to specific tissues and cells. The composition comprises microparticles containing a biocompatible polymer, a water-soluble polymer and a biologically active agent. In one embodiment, the biologically active agent is an antigen or an immunomodulator. In another embodiment, the biologically is a labile agent. The microparticles have a number median diameter of greater than 20 microns upon administration. The water-soluble polymer is present in the sustained released composition in at least about 20% of the dry weight of the microparticle. The sustained release composition provides for the dissolution of the water-soluble polymer of the composition upon hydration, at a much greater rate than the degradation of the biocompatible polymer. This variance in solubility generates pseudo-microparticles which have a number median diameter which is substantially smaller than the size of the administered microparticles. The pseudo-microparticles can be engulfed by antigen presenting cells of the immune system, or absorbed by the Peyer's patches in the gut.

45 Claims, 2 Drawing Sheets

U.S. PATENT DOCUMENTS

| | | |
|---|---|---|
| 5,603,961 A | 2/1997 | Suzuki et al. |
| 5,733,567 A | 3/1998 | Arola et al. |
| 5,811,128 A | 9/1998 | Tice et al. |
| 5,814,344 A | 9/1998 | Tice et al. |
| 5,840,322 A | 11/1998 | Weiss et al. |
| 5,853,763 A | 12/1998 | Tice et al. |
| 5,869,103 A | 2/1999 | Yeh et al. |
| 5,942,252 A | 8/1999 | Tice et al. |
| 6,015,576 A | 1/2000 | See et al. |
| 6,020,004 A | 2/2000 | Shah |
| 6,024,983 A | 2/2000 | Tice et al. |
| 6,113,947 A * | 9/2000 | Cleland et al. ............ 424/489 |

FOREIGN PATENT DOCUMENTS

| | | |
|---|---|---|
| WO | WO 89/08449 | 9/1989 |
| WO | WO 90/13285 | 11/1990 |
| WO | WO 90/13780 | 11/1990 |
| WO | WO 94/07469 | 4/1994 |
| WO | WO 95/11010 | 4/1995 |
| WO | WO 96/31202 | * 10/1996 |
| WO | WO 97/42940 | 11/1997 |
| WO | WO 00/72830 A1 | 12/2000 |
| WO | WO 01/58474 | 8/2001 |

OTHER PUBLICATIONS

Eldridge, J.H., et al., "Biodegradable Microspheres: Vaccine Delivery System for Oral Immunization," *Current Topics in Microbiology and Immunology*, 146:60-65 (1989).

Mullerad, J., et al., "Delivery of IL-1 Microspheres to Tumor Macrophages," *Proceed. Intern. Symp. Control. Rel. Bioact. Mater.*, 22:512-513 (1995).

Preis, I., and Langer, R.S., "A Single-Step Immunization by Sustained Antigen Release," *Journal Immunological Methods*, 28:193-197 (1979).

Tabata, Y., and Ikada, Y., "Phagocytosis of Polymer Microspheres by Macrophages," *Adv. Polym. Sci.*, 94:110-141 (1990).

Yan, C., et al., "Characterization and Morphological Analysis of Protein-loaded Poly (lactide-co-glycolide) Microparticles Prepared by Water-in-oil-in-water Emulsion Technique," *Journal of Controlled Release*, 32:231-241 (1994).

* cited by examiner

METHODS AND COMPOSITIONS FOR THE TARGETED DELIVERY OF BIOLOGICALLY ACTIVE AGENTS

RELATED APPLICATION

This application is a continuation of U.S. application Ser. No. 09/644,631, filed Aug. 23, 2000, now U.S. Pat. No. 6,565,888, issued on May 20, 2003. The entire teachings of the above application are incorporated herein by reference.

BACKGROUND OF THE INVENTION

Antigen-containing sustained release devices, such as polymer-based devices and liposomes, can be administered to effectively stimulate an immune response. The devices, however, must be of a size sufficient to permit an antigen presenting cell, such as a macrophage, to engulf and then process the antigen for presentation to T lymphocytes. See, for example, U.S. Pat. Nos. 5,942,252, 6,024,983, 5,811, 128, 5,814,344, and 5,853,763 to Tice et al., U.S. Pat. No. 6,015,576 to See et al. and Tabata, Y. and Ikada, Y., "Phagocytosis of Polymer Microspheres by Macrophages" *Adv. Polym. Sci.* 1990, 94, 110–141, the entire contents of which are hereby incorporated by reference. Another method of delivery in which the size of the delivery device is critical, is the systemic delivery of efficacious levels of drugs by absorption of drug-containing delivery devices in the Peyer's patches of the gastrointestinal tract. This need for small delivery devices, presents difficulties and disadvantages in both processing and handling of these devices. Therefore, a need exists for improved methods and compositions for targeted delivery of biologically active agents where a small delivery device is needed to obtain delivery of sufficient levels of the agent.

SUMMARY OF THE INVENTION

The present invention relates to a sustained release composition for the targeted delivery of biologically active agents to specific tissues and cells. The composition comprises microparticles containing a biocompatible polymer, a water-soluble polymer and a biologically active agent. In one embodiment, the biologically active agent is an antigen. In another embodiment, the biologically active agent is a labile agent. In yet another embodiment, the biologically active agent is an immunomodulator. The microparticles have a number median diameter of greater than 20 microns upon administration. The water-soluble polymer can be present in the sustained released composition in at least about 20% of the dry weight of the microparticle. For example, the water-soluble polymer can be present in the sustained release composition at about 30% or more such as 40% or more of the dry weight of the microparticles. In a particular embodiment, the water-soluble polymer is present from about 40% to about 60% of the dry weight of the microparticles, such as from about 40% to 50%.

It has been found that the characteristics of the sustained release composition provide for the dissolution of the water-soluble polymer of the composition upon hydration, at a much greater rate than the degradation of the biocompatible polymer. This variance in solubility generates pseudo-microparticles which have a number median diameter which is substantially smaller than the size of the administered microparticles. For example, the pseudo-microparticles can have a number median diameter of less than about 20 microns such as less than about 10 microns. Preferably, the number median diameter of the pseudo-microparticles is less than about 5 microns, for example, from about 1 to about 5 microns. The pseudo-microparticles can be engulfed by antigen presenting cells of the immune system, or absorbed by the Peyer's patches in the gut. The generation of pseudo-microparticles following administration, therefore overcomes the problems associated with the processing and handling of small microparticles, for example, microparticles having a number median diameter of less than about 20 microns.

The sustained release composition can be used in a method for stimulating a systemic immune response in a mammal. As such, the invention relates to a method for stimulating a systemic immune response in a mammal. The method comprises administering to a mammal an effective amount of a sustained release composition comprising microparticles containing an antigen, a biocompatible polymer, and a water-soluble polymer wherein, the microparticles have a number median diameter of greater than about 20 microns, the water-soluble polymer represents at least about 20% of the dry weight of the microparticles such as 30% or more, for example 40% or more, such as from about 40% to about 60%, for example from about 40% to about 50%, and the microparticles generate pseudo-microparticles upon hydration, whereby sufficient pseudo-microparticles can be taken up by antigen presenting cells to stimulate a systemic immune response. Administration can be by any route which provides interaction between the antigen presenting cells and the pseudo-microparticles.

The sustained release composition can also be used in a method for modulating an immune response in a mammal. As such, the invention relates to a method for modulating an immune response in a mammal. The method comprises administering to a mammal an effective amount of a sustained release composition comprising microparticles containing an immunomodulator, a biocompatible polymer, and a water-soluble polymer wherein, the microparticles have a number median diameter of greater than about 20 microns, the water-soluble polymer represents at least about 20% of the dry weight of the microparticles, for example, 30% or more such as 40% or more, for example, from about 40% to about 60%, such as from about 40% to about 50%, and the microparticles generate pseudo-microparticles upon hydration, whereby sufficient pseudo-microparticles can be taken up by antigen presenting cells to modulate an immune response, such as an autoimmune response. Administration can be by any route which provides interaction between the antigen presenting cells and the pseudo-microparticles containing the immunomodulator.

Further, the sustained release composition can be used in a method for the systemic delivery of efficacious levels of labile agents to a mammal by uptake into the Peyer's patches of the gastrointestinal tract. As such, the invention further relates to a method for the systemic delivery of an effective amount of a labile agent to a mammal by uptake into the Peyer's patches of the gastrointenstinal tract. The method comprises orally administering to the mammal an effective amount of the sustained release composition comprising microparticles containing a labile agent, a biocompatible polymer, and a water-soluble polymer wherein, the microparticles have a number median diameter of greater than 20 microns, the water soluble polymer represents at least about 20% of the dry weight of the microparticles and the microparticles generate pseudo-microparticles upon hydration, whereby sufficient pseudo-microparticles can be taken up into the Peyer's patches of the gastrointestinal tract.

The method of the invention for preparing a sustained release composition for the targeted delivery of a biologically active agent, comprises the steps of:
(a) forming a mixture comprising a labile agent or antigen, a biocompatible polymer, a water-soluble polymer and a solvent for the water soluble polymer and biocompatible polymer; and
(b) removing the solvent thereby forming a solid polymer/active agent matrix.

In a particular embodiment, the method can further comprise the step of forming droplets of the mixture prior to removal of the solvent. Further, the method can comprise freezing the droplets prior to removal of the solvent. According to the method of the invention, the droplets can be microdroplets. In a specific embodiment wherein droplets are formed of the mixture and then frozen, the solvent can be removed by an evaporation and/or extraction process.

DETAILED DESCRIPTION OF THE INVENTION

Figure 1:
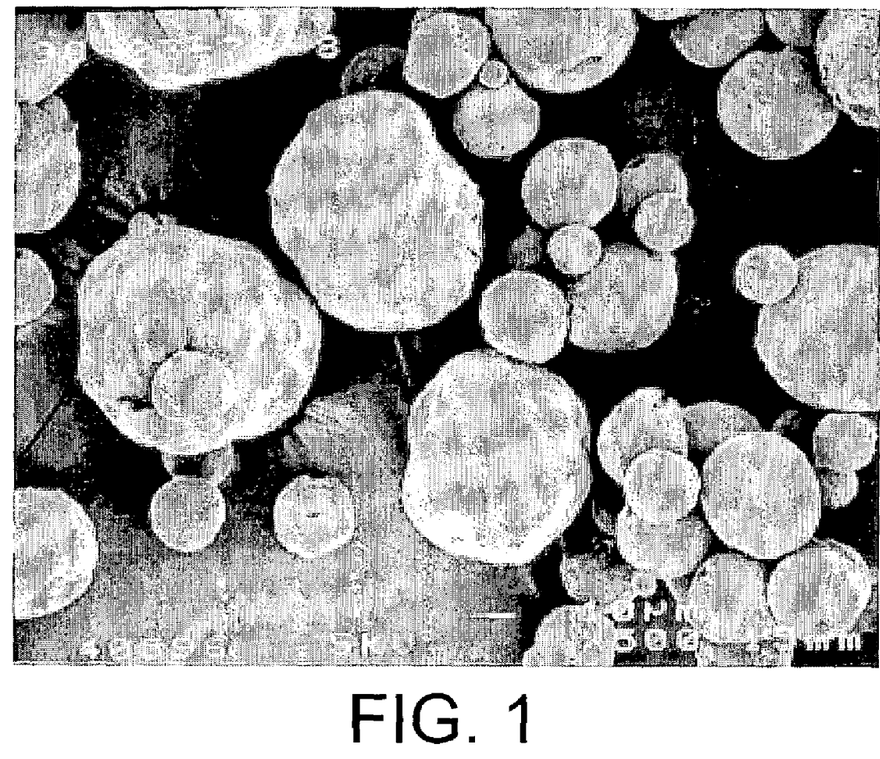
FIG. 1 shows a Scanning Electron Micrograph (SEM) of microparticles containing PLG, trehalose and the water soluble polymer F127 (40% w/w), prepared as described herein. The particles have a measured number median diameter of about 47.6 μm.
Figure 2:
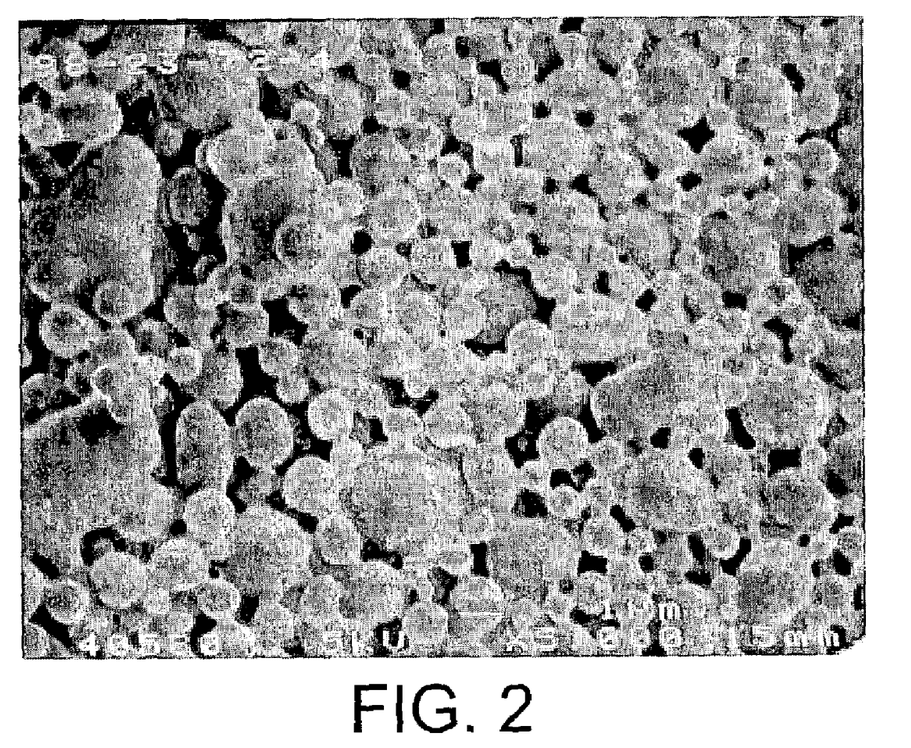
FIG. 2 is an SEM of the pseudo-microparticles generated upon hydration of the microparticles shown in FIG. 1. The microparticles were hydrated at 37° C. for 2 hours in pH 7.2 PBS. After incubation the buffer was removed and the microparticles dried by lyophilization. The pseudo-microparticles have a measured number median diameter of about 1.4 μm.

The foregoing and other objects, features and advantages of the invention will now be more particularly described with reference to the accompanying drawings and pointed out in the claims. It is understood that the particular embodiment of the invention are shown by way of illustration and not as limitations of the invention. The principles of the invention can be employed in various embodiments without departing from the scope of the invention. A description of the preferred embodiments of the invention follows.

The sustained release composition of the invention comprises microparticles containing a biocompatible polymer, a water-soluble polymer and a biologically active agent. The microparticles have a number median diameter of greater than 20 microns upon administration. The water-soluble polymer is present in the sustained released composition in at least about 20% of the dry weight of the microparticle, for example, 30% or more such as at about 40% or more, for example, from about 40% to about 60%, such as from about 40% to about 50%. The presence of the water soluble polymer in at least about 20% of the dry weight of the microparticle, for example, 40% or more, provides for the dissolution of the water-soluble polymer of the composition upon hydration in vivo at a much greater rate than the degradation of the biocompatible polymer. The biocompatible polymer can be water-insoluble or minimally water-soluble. This variance in solubility between the biocompatible polymer and the water-soluble polymer results in the generation of pseudo-microparticles upon hydration in vivo. The pseudo-microparticles have a number median diameter which is substantially smaller than the size of the administered microparticles. For example, the pseudo-microparticles can have a number median diameter of less than about 20 microns, such as less than about 10 microns. Preferably, the number median diameter of the pseudo-microparticles is less than about 5 microns, for example, from about 1 micron to about 5 microns. As such, the need for the preparation and handling of small microparticles, for example, less than about 20 microns is overcome.

"Pseudo-microparticles" as that term is used herein refers to the particles which are generated upon hydration in vivo of the administered sustained release composition. The pseudo-microparticles have a number median diameter of less than about 20 microns, such as less than about 10 microns. Preferably, the pseudo-microparticles have a number median diameter of less than about 5 microns, for example, from about 1 to about 5 microns. The pseudo-microparticles comprise the biocompatible polymer and labile agent, antigen or immunomodulator which is present in the microparticles of the sustained release composition. It is possible that a residual amount of the water-soluble polymer present in the administered microparticles of the sustained release composition is also present in the pseudo-microparticles. However, it is believed that the generation of the pseudo-microparticles is caused by the dissolution of a substantial portion of the water-soluble polymer.

In one embodiment, the biologically active agent of the sustained release composition is an antigen and the composition can be administered to stimulate a systemic immune response. In another embodiment, the biologically active agent of the sustained release composition is an immunomodulator and the composition can be administered to modulate an immune response. In these embodiments, the pseudo-microparticles can be absorbed by antigen presenting cells such as macrophages and dendritic cells. Administration can be by any route (e.g., orally or parenterally, such as by inhalation or injection) which provides interaction between the antigen presenting cells and the pseudo-microparticles. For example, liver macrophages also referred to as Kupffer cells can absorb the pseudo-microparticles of the sustained release composition. Similarly, the aveolar macrophages of the lung, the macrophages of the brain, typically referred to as microglial cells, and the splenic macrophages commonly referred to as lymphoid macrophages can also absorb the pseudo-microparticles resulting from the administration of the sustained release composition described herein. In addition, the pseudo-microparticles can be absorbed by the Peyer's patches of the gut and taken up by the macrophages therein.

"Antigen-presenting cell" as that term is used herein, includes cells of the immune system capable of digesting antigen and displaying the antigen in conjunction with the major histocompatibility complex II (MHC II) glycoproteins to T-helper cells. For example, macrophages and dendritic cells are antigen presenting cells. The T-helper cells activate B cells which proliferate and differentiate into mature plasma cells that secrete immunoglobulins. Typically in the systemic response, the immunoglobulins initially secreted are IgM followed by an isotype switch to IgG.

In the present invention, the antigen presenting cells, such as macrophages or dendritic cells, after taking up the pseudo-microparticles digest the pseudo-microparticles and the incorporated antigen is released. The internalized antigen is then processed, and presented or displayed at the surface of the macrophage or dendritic cell in conjunction with the major histocompatibility complex II (MHC II) glycoproteins to T-helper cells. T-helper cells activate B cells which proliferate and differentiate into mature plasma cells that secrete copious amounts immunoglobulins.

When the incorporated biologically active agent is an immunomodulator, such as an immunosuppressant, the macrophages or dendritic cells can take up the pseudo-microparticles and the incorporated immunomodulator can be released therein. As such, the sustained release composition having an immunomodulator incorporated therein can be useful in the treatment of autoimmune diseases, such as systemic lupus erythematosus and multiple sclerosis, by rendering the absorbing macrophage less responsive. In addition, the sustained release composition having an immunomodulator such as an anergizing agent or a tolerance inducing agent, can be administered for the treatment of autoimmune diseases where anergy or tolerance induction can be effective. Such anergizing agents and tolerance inducing agents can also be useful for the treatment of conditions exascerbated by the activity of macrophages, such as schistosomiasis.

Peyer's patches are one of two types of lymphoid aggregates referred to as gut-associated lymphoid tissue (GALT). Peyer's patches have a defined microstructure including a central B cell dependent follicle and T cell dependent regions adjacent to the follicle. The lymphocytes in Peyer's patches are heterogeneous, including B cells which express IgM, IgG, IgA and IgE and various regulatory and cytotoxic T cells. Peyer's patches also contain specialized macrophages. The Peyer's patches are covered by M cells which are specialized lympho-epithelium cells.

The absorption of antigens by the Peyer's patches can result in a local or a systemic immune response. In a systemic immune response the antigens are absorbed by the Peyer's patches and taken up by macrophages therein. The macrophages induce a systemic response by processing antigens and presenting them to lymphocytes. The lymphocytes then become activated and cause the production of systemic antibodies specific to the antigens.

In a local immune response the antigens are absorbed by the Peyer's patches and taken up by the M cells which deliver the antigen to the underlying lymphocytes in the tissue. This results in the production of IgA at various secretory effector sites following the migration of activated lymphocytes through the efferent, lymphatic and circulatory system.

In addition, the Peyer's patches are able to absorb pseudo-microparticles containing labile agent wherein the labile agent is released and transported into the blood stream via the lymphatic system. As such, in another embodiment, the biologically active agent of the sustained release composition is a labile agent and the composition is orally administered. In this embodiment, the pseudo-microparticles generated upon hydration are of a sufficient size to be absorbed by the Peyer's patches of the gastrointestinal tract. Following absorption by the Peyer's patches, the labile agent incorporated within the pseudo-microparticles can be released and transported into the blood stream via the lymphatic system.

As used herein, "systemic immune response" refers to whole body production and circulation or organism specific immune cells. The response is characterized by organism specific immunoglobulin (antibodies) and cytotoxic mononuclear cells. A systemic immune response provides specific subsequent responses to the same stimulus.

As used herein, "sufficient pseudo-microparticles to stimulate an immune response" means that amount of antigen-containing pseudo-microparticles that effect a detectible immune response, preferably a therapeutic response. A systemic immune response can be confirmed by neutralizing antibody testing or other means of specific antibody testing, as is well known in the art.

As used herein, "sufficient pseudo-microparticles to modulate an immune response" means that amount of immunomodulator-containing pseudo-microparticles that effect a modulation of an immune response. A modulation of the immune response can be confirmed by appropriate monitoring of the patient's serum such as by specific antibody testing, as is well known in the art.

As used herein, "sufficient pseudo-microparticles are absorbed into the Peyer's patches" means that amount of active agent-containing pseudo-microparticles that results in detectable serum levels of the active agent for a sustained period. Preferably the active agent is a labile agent.

The pseudo-microparticles produced in vivo from the administered sustained release composition can be of various sizes allowing antigens to be released in the macrophages over a long period of time resulting in continued stimulation of a systemic immune response over a period of time. The smaller sized pseudo-microparticles are taken up by the macrophages relatively quickly and provide an immediate systemic immune response. Medium sized pseudo-microparticles are taken up by the macrophages, at a slower pace. Taken in combination, these medium sized pseudo-microparticles can act as a booster. The larger sized pseudo-microparticles take even longer to be taken up by the macrophages and, when taken in combination, act as a second booster. Hence, use of a sustained release composition which generates pseudo-microparticles of varying sizes following administration of the sustained release composition described herein, can provide a single dose of the antigen-containing microparticles which can be sufficient to result in long term and even permanent immunity to the incorporated antigen.

As used herein, the term "antigen" may be any substance which, when introduced into a mammal, will induce a detectable immune response. As such, the term includes any portion of an antigen, for example, the epitope which can induce an immune response. In a particular embodiment, the antigen is an attenuated or killed microorganism, such as a virus or bacteria.

Antigens which can be incorporated into the sustained release composition to stimulate a systemic immune response include, but are not limited to antigens to vaccinate against viral, bacterial, protozoan and fungal diseases and pathogens. Examples of diseases and pathogens to which antigens can be used to vaccinate against include, but are not limited to, polio virus, such as, polio 1, 2, 3; hepatitis, such as, hepatitis A through II; Coxsackie, such as, Coxsackie B1–B6; mumps; measles, rubella; respiratory syncytial (RS) virus; parainfluenze, such as, parainfluenza 1–4; influenza A, B and C; Hemophilus influenza; Bordetella pertussis, Neisseria gonorrhoeae; adenovirus, such as, types 1–41; Mycoplasma pneumonia; Streptococcus pneumonia; Chlamydia trachomatis; pneumoniae and psittacocci; malaria; Mycobacterium tuberculosis, *Pseudomonas* species, *Escherichia coli* species, *salmonella* species, *Trypanasoma cruzi* species; *Plasmodium falciparum*; helminthic pathogens; yellow fever virus and *vibrio cholerae* species. Antigens to vaccinate against allergens are also suitable for incorporation into the sustained release composition. Allergens include, but are not limited to, plant pollens, drugs, foods, venoms, insect excretions, molds, animal fluids, and animal hair and dander. Particular plant pollens include, for example, ragweed, trees, grass, flowers and ferns.

In a specific embodiment, the antigen is a DNA-based vaccine such as a plasmid DNA. Use of such plasmid-encoded antigens is known in the art. See, for example, Hedley, M. L. et al. "Microspheres Containing Plasmid Encoded Antigens Elicit Cytotoxic T-Cell Responses" *Nature Med.* 1998, 4, 365–368; Ando, S. et al., "PLGA Microspheres Containing Plasmid DNA: Preservation of Supercoiled DNA Via Cryopreparation and Carbohydrate Stabilization", *Journal of Pharmaceutical Sciences*, Vol. 88, No. 1, January 1999; and Ciftci, K., et al. "Polymer Based Gene Delivery Systems: An Effective Way to Introduce DNA Into Mammalian Cells", *Pharm. Res.*, 1997, 14, 5639 the entire contents of all of which is incorporated herein by reference.

It is understood that various combinations of antigens can be incorporated into the microparticles. Further, if desired a therapeutic drug and/or a cytokine can also be incorporated with the antigen.

In yet another embodiment, the administration of a combination of antigen and cytokine can be used to stimulate a systemic immune response. In one embodiment, the cytokine and antigen are co-incorporated into the microparticles of the sustained release composition. In another embodiment, the cytokine and antigen are incorporated into separate microparticles of the sustained release composition. When the cytokine and antigen are present in separate microparticles, administration can be simultaneous or sequential in any order. However, the separate microparticles must be administered sufficiently close in time such that the antigen and cytokine are encountered by the mammal's immune system together.

As used herein, the term "cytokine" refers to the general class of hormones of the cells of the immune system, such as lymphokines, cytokines and monokines. The definition includes, but is not limited to, those hormones that act locally and do not circulate in the blood and which, when used in accord with the present invention will assist in stimulation of a systemic immune response. Examples of suitable cytokines include, the interluekins (IL), such as, IL-1 (α or β), IL-2, IL-3, IL-4, IL-5, IL-6, IL-7, IL-8, IL-9, IL-10, IL-11, IL-12, GM-CSF, M-CSF, LIF, LT, TGF-β, γ-IFN, α-IFN, β-IFN, TNF-α, BCGF, CD2, ICAM, MAd-CAM, MCP-1, MCP-2, MCP-3.

A "labile agent" as that term is used herein, is a protein, polypeptide or oligonucleotide, or the pharmaceutically acceptable salt thereof, which is in its molecular, biologically active form when released in vivo, thereby possessing the desired therapeutic, prophylactic and/or diagnostic properties in vivo. It is understood that the labile agent can be a stabilized labile agent as described herein. Suitable proteins include, but are not limited to, immunoglobulins, antibodies, cytokines (e.g., lymphokines, monokines, chemokines), interluekins, interferons, erythropoietin, nucleases, tumor necrosis factor, colony stimulating factors, insulin, enzymes (e.g., superoxide dismutase, a plasminogen activator), tumor suppressors, blood proteins, hormones and hormone analogs (e.g., a growth hormone such as, human growth hormone (hGH), adrenocorticotropic hormone, leutinizing hormone releasing hormone (LHRH)), vaccines (e.g., tumoral, bacterial and viral antigens), antigens, growth factors and blood coagulation factors. Suitable polypeptides include protein inhibitors, protein antagonists, and protein agonists.

Examples of oligonucleotides suitable for use in the invention include, but are not limited to, nucleic acids, such as ribonucleic acids and deoxyribonucleic acids, antisense molecules, ribozymes, antisense oligonucleotides, peptide nucleic acids, decoy RNAs and "dumbbell" DNAs also known as transcription factor decoy DNAs.

As used herein, the term "immunomodulator" refers to agents which can modulate an immune response following engulfment of a sustained release composition containing the immunomodulator by a antigen-presenting cell such as a macrophage. For example, cytokines, which can assist in stimulating an immune response or immunosuppressants, which can be used to treat autoimmune diseases are suitable immunomodulators. As such, immunomodulators include, but are not limited to, cyclosporin, ricin, FK506, rapamycin and analogs and derivatives thereof. In addition, an immunomodulator can be an anergizing agent or a tolerance inducing agent.

As used herein, the term "particle size" refers to a number median diameter as determined by conventional particle size measuring techniques known to those skilled in the art, such as, laser diffraction, photon correlation spectroscopy, sedimentation field flow fractionation, disk centrifugation or electrical sensing zone method. Laser diffraction is preferred. The "number median diameter" reflects the distribution of particles (by number) as a function of particle diameter. An alternative designation of particle size often used in the art is the "volume median diameter". The volume median diameter is the median diameter of the volume weighted size distribution, also referred to as $D_{v,50}$. The volume median diameter reflects the distribution of volume as a function of particle diameter.

As used herein, the term "microparticles" refers to particles having a number median diameter of greater than 20 microns. In a particular embodiment, the microparticles have a number median diameter of greater than 50 microns. For example, from about 50 microns to about 200 microns.

A "water-soluble polymer" as defined herein is any polymer which is soluble in water or an aqueous-based system. For purposes of this invention, the water-soluble polymer is also soluble in the solvent for the biocompatible polymer used in the process for preparing the sustained release composition described herein. Water-soluble polymers suitable for use in the invention include water-soluble polysaccharides, for example, ficoll and polymer surfactants, in particular, nonionic polymer surfactants. Suitable nonionic polymer surfactants include poloxamers, which are polyethylenepolypropyleneglycol polymers commonly referred to as Pluronics. For example poloxamer 407 sold under the trademark PLURONIC F127, poloxamer 188 sold under the trademark PLURONIC F68 (available from BASF Wyandotte) and combinations thereof. Polysorbates are another type of nonionic surfactant often referred to as polyoxyethylene sorbitan esters. Polysorbate 80 sold under the trademark TWEEN® 80, polysorbate 20 sold under the trademark TWEEN® 20 and combinations thereof are suitable polysorbates for use as the water soluble polymer of the invention. Other water-soluble nonionic polymer surfactants suitable for use in the invention include, but are not limited to, polyethylene glycol polymers, polyvinylpyrrolidones, and any combinations of any of the above.

The amount of water-soluble polymer which can be present in the sustained release composition is preferably at least about 20% (w/w), more preferably 40% or more, such as from about 40% (w/w) to about 60% (w/w) of the dry weight of the sustained release composition. In a specific embodiment, the range is from about 40% (w/w) to about 50% (w/w). However, it is understood that the amount of water-soluble polymer needed can be determined by preparing a microparticle formulation, subjecting the formulation to hydration in vitro as described herein and determining the particle size following hydration by available methods, such as SEM or particle size analysis. As such, the amount of water-soluble polymer needed can in some formulations, be determined to be less than about 20%.

The term "sustained release composition" as defined herein, comprises a biocompatible polymer, an antigen or a labile agent, and a water-soluble polymer dispersed throughout the biocompatible polymer.

The polymers of the invention are biocompatible. Suitable biocompatible polymers, can be either biodegradable or non-biodegradable polymers or blends or copolymers thereof, as described herein. The biocompatible polymers suitable for use in the invention can therefore be water-insoluble or minimally water-soluble. Generally, the biocompatible polymer is less water soluble or solubilizes at a slower rate than the water-soluble polymer present in the sustained release composition.

As defined herein, a sustained release of biologically active agent is a release of the agent from the sustained release composition of the invention which occurs over a period which is longer than that period during which a biologically significant amount of the agent would be available following direct administration of a solution of the agent. It is preferred that a sustained release be a release of agent which occurs over a period of greater than two days. A sustained release of agent from a polymeric matrix can be a continuous or a discontinuous release, with relatively constant or varying rates of release. The continuity of release and level of release can be affected by the type of polymer composition used (e.g., monomer ratios, molecular weight, block composition, and varying combinations of polymers), protein loading, and/or selection of excipients to produce the desired effect.

Suitable biocompatible polymers, can be either biodegradable or non-biodegradable polymers or blends or copolymers thereof, as described herein. The biocompatible polymer is preferably water insoluble or at least minimally water soluble. Generally, it is less water soluble or solubilizes at a slower rate than the water soluble polymer also present in the sustained release composition. In addition, the biocompatible polymer, generally, degrades at a slower rate than the water soluble polymer solubilizes. Further, a mixture of a rapidly degrading biocompatible polymer and a biocompatible polymer which degrade more slowly can be envisioned as suitable for targeted delivery to specific tissues and cells. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl fluoride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons.

In a particular embodiment, the polymer is biodegradable polymer or copolymer. In a more preferred embodiment, the polymer is a poly(lactide-co-glycolide) (hereinafter "PLG"). The PLG can have a lactide:glycolide ratio, for example, of about 10:90, 25:75, 50:50, 75:25 or 90:10 and a molecular weight of about 5,000 Daltons to about 70,000 Daltons.

An enteric coating can be applied to the sustained release composition to prevent degradation in the stomach when administration is by the oral route. Suitable enteric coating compositions include, but are not limited to, alkyl and hydroxyalkyl celluloses and their aliphatic ester, e.g., methylcellulose, ethylcellulose, hydroxyethylcellulose, hydroxypropylcellulose, hydroxybutylcellulose, hydroxyethylcellulose, hydroxypropylmethylcellulose, hydroxybutylmethylcellulose, hydroxypropylcellulose phthalate, hydroxypropylmethylcellulose phthalate and hydroxypropylmethylcellulose acetate succinate; carboxyalkylcelluloses and their salts, e.g., carboxymethylethylcellulose; cellulose acetate phthalate; polycarboxymethylene and its salts and derivatives; polyvinylalcohol and its esters, polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oil; polyvinylpyrrolidone; polyethyleneglycol and it esters.

The term "biologically active agent," as used herein, is an agent, such as an antigen or a labile agent, or its pharmaceutically acceptable salt, which when released in vivo, possesses the desired biological activity, for example immunologic, therapeutic, diagnostic and/or prophylactic properties in vivo. It is understood that the term includes stabilized biologically active agents as described herein.

A sustained release composition of the invention can contain from about 0.01% (w/w) to about 30% (w/w) of active agent (dry weight of composition). The amount of agent can vary depending upon the desired effect of the agent, the planned release levels, and the time span over which the agent is to be released. A preferred range of agent loading is between about 0.1% (w/w) to about 30% (w/w). A more preferred range of agent loading is between about 0.5% (w/w) to about 10% (w/w) agent.

In one embodiment, the biologically active agent, such as an antigen or labile agent, is stabilized. The biologically active agent can be stabilized against degradation, loss of potency and/or loss of biological activity, all of which can occur during formation of the sustained release composition having the biologically active agent dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent or a specific combination of stabilizing agents. The stabilizing agent can be present in the mixture. "Stabilizing agent", as that term is used herein, is any agent which binds or interacts in a covalent or non-covalent manner or is included with the biologically active agent. Stabilizing agents suitable for use in the invention are described in U.S. Pat. Nos. 5,716,644, 5,674,534, 5,654,010, 5,667,808, and 5,711,968, and co-pending U.S. patent application Ser. No. 08/934,830 to Burke et al., filed on Sep. 22, 1997 and Ser. No. 09/104,549 to Burke, filed on Jun. 25, 1998 the entire teachings of which are incorporated herein by reference.

For example, a metal cation can be complexed with the biologically active agent, or the biologically active agent can be complexed with a polycationic complexing agent such as protamine, albumin, spermidine and spermine, or associated with a "salting-out" salt. In addition, a specific combination of stabilizing agents and/or excipients may be needed to optimize stabilization of the biologically active agent.

Suitable metal cations include any metal cation capable of complexing with the biologically active agent. A metal cation-stabilized biologically active agent, as defined herein, comprises a biologically active agent and at least one type of metal cation wherein the cation is not significantly oxidizing to the biologically active agent. In a particular embodiment, the metal cation is multivalent, for example, having a valency of +2 or more. It is preferred that the metal cation be complexed to the biologically active agent.

Suitable stabilizing metal cations include biocompatible metal cations. A metal cation is biocompatible if the cation is non-toxic to the recipient, in the quantities used, and also presents no significant deleterious or untoward effects on the recipient's body, such as a significant immunological reaction at the injection site. The suitability of metal cations for stabilizing biologically active agents and the ratio of metal cation to biologically active agent needed can be determined by one of ordinary skill in the art by performing a variety of stability indicating techniques such as polyacrylamide gel electrophoresis, isoelectric focusing, reverse phase chromatography, and HPLC analysis on particles of metal cation-stabilized biologically active agents prior to and following particle size reduction and/or encapsulation. The molar ratio of metal cation to biologically active agent is typically between about 1:2 and about 100:1, preferably between about 2:1 and about 12:1.

Examples of stabilizing metal cations include, but are not limited to, $K^+$, $Zn^{+2}$, $Mg^{+2}$ and $Ca^{+2}$. Stabilizing metal cations also include cations of transition metals, such as $Cu^{+2}$. Combinations of metal cations can also be employed.

The biologically active agent, such as an antigen or labile agent, can also be stabilized with at least one polycationic complexing agent. Suitable polycationic complexing agents include, but are not limited to, protamine, spermine, spermidine and albumin. The suitability of polycationic complexing agents for stabilizing biologically active agents can be determined by one of ordinary skill in the art in the manner described above for stabilization with a metal cation. An equal weight ratio of polycationic complexing agent to biologically active agent is suitable.

Further, excipients can be added to maintain the potency of the biologically active agent over the duration of release and modify polymer degradation. The excipients can be added to the dispersed system which is then atomized or can be added to the mixture which is subjected to fragmenting either before or after fragmentation of the dried substance to achieve particles of biologically active agent. Suitable excipients include, for example, carbohydrates, amino acids, fatty acids, surfactants, and bulking agents, and are known to those skilled in the art. An acidic or a basic excipient is also suitable. The amount of excipient used is based on ratio to the biologically active agent, on a weight basis. For amino acids, fatty acids and carbohydrates, such as sucrose, trehalose, lactose, mannitol, dextran and heparin, the ratio of carbohydrate to biologically active agent, is typically between about 1:10 and about 20:1. For surfactants the ratio of surfactant to biologically active agent is typically between about 1:1000 and about 2:1. Bulking agents typically comprise inert materials. Suitable bulking agents are known to those skilled in the art.

The excipient can also be a metal cation component which is separately dispersed within the polymer matrix. This metal cation component acts to modulate the release of the biologically active agent and is not complexed with the biologically active agent. The metal cation component can optionally contain the same species of metal cation, as is contained in the metal cation stabilized biologically active agent, if present, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3.Mg(OH)_2.5H_2O$), $MgSO_4$, $Zn(OAc)_2$, $Mg(OAc)_2$, $ZnCO_3$ (such as $3Zn(OH)_2.2ZnCO_3$)$ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a biologically active agent from the polymer matrix is further described in U.S. Pat. No. 5,656,297 to Bernstein et al. and co-pending U.S. patent application Ser. No. 09/056,566 filed on Apr. 7, 1998, the teachings of both of which are incorporated herein by reference in their entirety.

A number of methods are known by which sustained release compositions (polymer/active agent matrices) can be formed. In many of these processes, the material to be encapsulated is dispersed in a solvent containing a wall forming material. At a single stage of the process, solvent is removed from the microparticles and thereafter the microparticle product is obtained.

Methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Without being bound by a particular theory it is believed that the release of the biologically active agent can occur by two different mechanisms. First, the biologically active agent can be released by diffusion through aqueous filled channels generated in the polymer matrix, such as by the dissolution of the biologically active agent, or by voids created by the removal of the polymer solvent during the preparation of the sustained release composition. A second mechanism is the release of the biologically active agent, due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer.

By altering the properties of the polymer, the contributions of diffusion and/or polymer degradation to biologically active agent release can be controlled. For example, increasing the glycolide content of a poly(lactide-co-glycolide) polymer and decreasing the molecular weight of the polymer can enhance the hydrolysis of the polymer and thus, provides an increased biologically active agent release from polymer erosion.

The composition of this invention can be administered in vivo, for example, to a human, or to an animal, orally, or parenterally such as by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of antigen or labile agent based on the known parameters for treatment with the particular agent of the various medical conditions.

As used herein, a "therapeutically effective amount", "prophylactically effective amount" or "diagnostically effective amount" is the amount of the sustained release composition needed to elicit the desired biological response following administration. For example the desired biological response can be the uptake of a sufficient amount of pseudo-microparticles needed to stimulate an immune response or modulate an immune response. The desired biological response can also be delivery of efficacious amount of a labile agent.

The invention will now be further and specifically described by the following examples which are not intended to be limiting.

EXEMPLIFICATION

Preparative Methods

Polymer

The polymer employed in the following examples was purchased from Alkermes, Inc. of Cincinnati, Ohio, and can be described as follows: poly(lactide-co-glycolide)(PLG); 50:50 lactide:glycolide ratio; 10 kD Mol. Wt.; esterified end groups (Cat. No. 50/502M).

General Process for Preparing Polymer/Active Agent Matrix Particles
 (a) Formation of a mixture comprising a biocompatible polymer, a water soluble polymer, a labile agent or antigen, and a solvent for the water soluble polymer and biocompatible polymer.
 (b) Optional homogenization of the mixture.
 (c) Atomization of the mixture to form droplets.
 (d) Freezing of the droplets by contact with liquid nitrogen.
 (e) Extraction of the polymer solvent from frozen droplets into an extraction solvent (e.g., −80° C. ethanol) thereby forming a solid polymer/active.
 (f) Isolation of the solid polymer/active agent matrix particles from the extraction solvent by filtration.
 (g) Removal of remaining solvent by evaporation.
(h) Optional sizing of particles by passage through an appropriately sized mesh.

Scanning Electron Microscopy:

Scanning electron microscopy was conducted using a JEOL Model 6400 at a voltage of 5 kV. Samples were held in place with double-sided carbon tape affixed to an aluminum stub and sputter coated with a layer of gold. Photographs were taken at a magnifications of 500× and 5,000×. An SEM of microparticles at 500× prepared according to the method outline above and further detailed in Example 1 are illustrated in FIG. 1. FIG. 2 is an SEM of the pseudo-microparticles at 5000× generated from the microparticles shown in FIG. 1 following hydration for two hours at 37° C. in pH 7.2 PBS (50 mM sodium phosphate, 100 mM NaCl, 0.02% sodium azide). After incubation, the buffer was removed and the microparticles were dried by lyophilization.

Example 1

Preparation of Trehalose Containing Microparticles

The polymer used in the example was purchased from Alkermes, Inc. of Cincinnati, Ohio, and is a poly(lactide-co-glycolide) (PLG); 50:50 lactide:glycolide ratio; 10 kD Mol. Wt.; esterified end groups.

Trehalose containing microparticles were prepared according to the process outlined above, using 10% w/v solution of the PLG and water soluble polymer F127 in methylene chloride, and a 1.0% w/v suspension of the 38 μm sieved trehalose in the polymer solution such that the final microparticles contain 40% w/w of the F127.

Example 2

Hydration of Microparticles

A portion of microparticles were incubated for 2 hours at 37° C. in pH 7.2 PBS (50 mM sodium phosphate, 100 mM NaCl, 0.02% sodium azide). After incubation, buffer was removed and the microparticles were dried by lyophilization.

Example 3

Particle Size Analysis

Particle size measurements of the microparticles and pseudo-microparticles of the invention were accomplished using a Coulter LS 130 Particle Size Analyzer (Model 130) equipped with the Small Volume Module. The data was deconvoluted to obtain the particle size distribution as the number median diameter using methylene chloride as the circulating fluid and the analysis software supplied with the unit.

Results of particle size analysis on the microparticles of Example 1 (pre-hydration) and following hydration (Example 2) are set forth below.

| | PARTICLE SIZE |
|---|---|
| SAMPLE | NUMBER MEDIAN DIAMETER |
| Pre-Hydration | 47.6 μm. |
| Post-Hydration | 1.4 μm. |

As can be seen the particle size measured as the number median diameter was less than 5 μm following hydration. The data is consistent with the particle sizes determined from the SEMs set forth in FIGS. 1 and 2.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the systemic delivery of an effective amount of a labile agent to a mammal comprising orally administering to the mammal an effective amount of a sustained release composition comprising microparticles containing a labile agent, a biocompatible polymer, and a water soluble polymer wherein, the microparticles have a number median diameter of greater than 20 microns, the water soluble polymer represents at least about 20% of the dry weight of the microparticles and the microparticles generate pseudo-microparticles upon hydration, whereby sufficient pseudo-microparticles are absorbed into the Peyer's patches of the gastrointenstinal tract.

2. The method of claim 1 wherein the labile agent is a protein, polypeptide or oligonucleotide.

3. The method of claim 1 wherein the labile agent is a protein.

4. The method of claim 1 wherein the labile agent is complexed to a stabilizing metal cation.

5. The method of claim 4 wherein said stabilizing metal cation is selected from the group consisting of $Zn^{+2}$, $Ca^{+2}$, $Cu^{+2}$, $Mg^{+2}$, $K^{+}$ and any combination thereof.

6. The method of claim 1 wherein the biocompatible polymer is biodegradable.

7. The method of claim 6 wherein the biodegradable polymer is selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

8. The method of claim 7, wherein said polymer is poly(lactide-co-glycolide).

9. The method of claim 1 wherein the composition for sustained release further comprises a metal cation component dispersed within the biocompatible polymer.

10. The method of claim 9 wherein the metal cation component is selected from the group consisting of Mg(OH)$_2$, MgCO$_3$, CaCO$_3$, ZnCO$_3$, Mg(OAc)$_2$, Zn(OAc)$_2$, ZnSO$_4$, MgCl$_2$, ZnCl$_2$, MgSO$_4$, zinc citrate and magnesium citrate.

11. The method of claim 5 wherein the sustained release composition is enterically coated.

12. The method of claim 5 wherein the water-soluble polymer is a nonionic surfactant.

13. The method of claim 12 wherein the nonionic surfactant is selected from the group consisting of: polyoxamers, polysorbates, polyethyleneglycols, polyvinylpyrrolidones and combinations thereof.

14. The method of claim 13 wherein the nonionic surfactant is a poloxamer and combinations thereof.

15. The method of claim 14 wherein the poloxamer is poloxamer 188, poloxamer 407 or any combination thereof.

16. The method of claim 13 wherein the nonionic surfactant is a polysorbate and combinations thereof.

17. The method of claim 16 wherein the polysorbate is polysorbate 80, polysorbate 20 or any combination thereof.

18. The method of claim 1 wherein the water-soluble polymer is present at about 40% or more of the dry weight of the microparticles.

19. The method of claim 18 wherein the water-soluble polymer is present from about 40% to about 60% of the dry weight of the microparticles.

20. The method of claim 18 wherein the water-soluble polymer is present from about 40% to about 50% of the dry weight of the microparticles.

21. A method for modulating an immune response in a mammal comprising administering to the mammal an effective amount of a sustained release composition comprising microparticles containing an immunomodulator, a biocompatible polymer, and a water soluble polymer wherein, the microparticles have a number median diameter of greater than 20 microns, the water soluble polymer represents at least about 20% of the dry weight of the microparticles and the microparticles generate pseudo-microparticles upon hydration whereby sufficient pseudo-microparticles are taken up by antigen presenting cells to modulate an immune response.

22. The method of claim 21 wherein the immunomodulator is a cytokine, immunosuppressant, anergizing agent or tolerance inducing agent.

23. The method of claim 22 wherein the immunosuppressant is cyclosporin, ricin, FK506, rapamycin and analogs and derivatives thereof.

24. A sustained release composition for oral administration to a mammal capable of delivering an effective amount of a labile agent comprising an effective amount of microparticles containing a labile agent, a biocompatible polymer, and a water soluble polymer wherein, the microparticles have a number median diameter of greater than 20 microns upon administration, the water soluble polymer represents at least about 20% of the dry weight of the microparticles and the microparticles hydrate in vivo to generate pseudo-microparticles having a number median diameter of less than about 20 microns.

25. The sustained release composition of claim 24 wherein the number median diameter of the pseudo-microparticles is about 10 microns or less.

26. The sustained release composition of claim 25 where the number median diameter of the pseudo-microparticles ranges from about 1 micron to about 5 microns.

27. The sustained release composition of claim 24 wherein the labile agent is a protein, polypeptide or oligonucleotide.

28. The sustained release composition of claim 24 wherein the labile agent is a protein.

29. The sustained release composition of claim 24 wherein the labile agent is complexed to a stabilizing metal cation.

30. The sustained release composition of claim 29 wherein said stabilizing metal cation is selected from the group consisting of Zn$^{+2}$, Ca$^{+2}$, Cu$^{+2}$, Mg$^{+2}$, K$^+$ and any combination thereof.

31. The sustained release composition of claim 24 wherein the biocompatible polymer is biodegradable.

32. The sustained release composition of claim 31 wherein the biodegradable polymer is selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

33. The sustained release composition of claim 32 wherein said polymer is poly(lactide-co-glycolide).

34. The sustained release composition of claim 24 further comprising a metal cation component dispersed within the biocompatible polymer.

35. The sustained release composition of claim 34 wherein the metal cation component is selected from the group consisting of Mg(OH)$_2$, MgCO$_3$, CaCO$_3$, ZnCO$_3$, Mg(OAc)$_2$, Zn(OAc)$_2$, ZnSO$_4$, MgCl$_2$, ZnCl$_2$, MgSO$_4$, zinc citrate and magnesium citrate.

36. The sustained release composition of claim 24 wherein the sustained release composition is enterically coated.

37. The sustained release composition of claim 24 wherein the water-soluble polymer is a nonionic surfactant.

38. The sustained release composition of claim 37 wherein the nonionic surfactant is selected from the group consisting of: poloxamers, polysorbates, polyethyleneglycols, polyvinylpyrrolidones and combinations thereof.

39. The sustained release composition of claim 38 wherein the nonionic surfactant is a poloxamer and combinations thereof.

40. The sustained release composition of claim 39 wherein the poloxamer is poloxamer 188, poloxamer 407 or any combination thereof.

41. The sustained release composition of claim 37 wherein the nonionic surfactant is a polysorbate and combinations thereof.

42. The sustained release composition of claim 41 wherein the polysorbate is polysorbate 80, polysorbate 20 or any combination thereof.

43. The sustained release composition of claim 24 wherein the water-soluble polymer is present at about 40% or more of the dry weight of the microparticles.

44. The sustained release composition of claim 43 wherein the water-soluble polymer is present from about 40% to about 60% of the dry weight of the microparticles.

45. The sustained release composition of claim 44 wherein the water-soluble polymer is present from about 40% to about 50% of the dry weight of the microparticles.

* * * * *